US008796343B2

(12) United States Patent
Champ et al.

(10) Patent No.: US 8,796,343 B2
(45) Date of Patent: Aug. 5, 2014

(54) USE OF WATER-ABSORBENT, PREDOMINANTLY OPEN-CELLED CROSSLINKED ACID-FUNCTIONAL ADDITION POLYMER FOAMS IN HYGIENE ARTICLES

(75) Inventors: Samantha Champ, Ludwigshafen (DE); Hans-Joachim Hähnle, Neustadt (DE); Mariola Wanior, Erlensee (DE)

(73) Assignee: BASF SE, Ludwigshafen (DE)

( * ) Notice: Subject to any disclaimer, the term of this patent is extended or adjusted under 35 U.S.C. 154(b) by 1334 days.

(21) Appl. No.: 12/260,399

(22) Filed: Oct. 29, 2008

(65) Prior Publication Data
US 2009/0045378 A1 Feb. 19, 2009

Related U.S. Application Data

(63) Continuation of application No. 10/520,545, filed as application No. PCT/EP03/07228 on Jul. 7, 2003, now abandoned.

(60) Provisional application No. 60/395,317, filed on Jul. 12, 2002.

(51) Int. Cl.
*C08J 9/12* (2006.01)
*C08J 9/30* (2006.01)

(52) U.S. Cl.
USPC ............... 521/51; 521/55; 521/63; 521/64; 521/65; 521/91; 521/142; 521/149

(58) Field of Classification Search
USPC ........... 521/51, 55, 63, 64, 65, 91, 142, 149
See application file for complete search history.

(56) References Cited

U.S. PATENT DOCUMENTS

| 4,286,082 | A | | 8/1981 | Tsubakimoto et al. |
| 4,734,478 | A | | 3/1988 | Tsubakimoto et al. |
| 5,372,766 | A | * | 12/1994 | Roe ............................. 264/126 |
| 5,387,207 | A | * | 2/1995 | Dyer et al. .................... 604/369 |
| 6,071,580 | A | * | 6/2000 | Bland et al. ................. 428/36.5 |
| 6,136,873 | A | | 10/2000 | Hahnle et al. |
| 6,245,410 | B1 | | 6/2001 | Hahnle et al. |
| 6,455,600 | B1 | | 9/2002 | Hahnle et al. |
| 6,750,262 | B1 | | 6/2004 | Hahnle et al. |
| 2002/0082311 | A1 | | 6/2002 | Dietzen et al. |

FOREIGN PATENT DOCUMENTS

| EP | 0 629 411 | 12/1994 |
| EP | 0 858 478 | 8/1998 |
| WO | WO-97/31600 | 9/1997 |
| WO | WO-99/44648 | 9/1999 |
| WO | WO-00/52087 | 9/2000 |
| WO | WO-00/71176 | 11/2000 |

OTHER PUBLICATIONS

International Search Report in WO 2004/007598 dated Nov. 27, 2003.

* cited by examiner

*Primary Examiner* — Irina S Zemel
(74) *Attorney, Agent, or Firm* — Marshall, Gerstein & Borun LLP

(57) ABSTRACT

Use in hygiene articles of articles formed of water-absorbent, predominantly open-celled crosslinked acid-functional addition polymer foams Abstract The use of articles formed of water-absorbent open-celled crosslinked acid-functional addition polymer foams and containing finely divided silicon dioxide and/or at least one surfactant on their surface as an acquisition and/or distribution layer in hygiene articles.

9 Claims, No Drawings

USE OF WATER-ABSORBENT, PREDOMINANTLY OPEN-CELLED CROSSLINKED ACID-FUNCTIONAL ADDITION POLYMER FOAMS IN HYGIENE ARTICLES

CROSS-REFERENCE TO RELATED APPLICATIONS

This is a continuation of U.S. patent application Ser. No. 10/520,545, filed Jan. 6, 2005 which is the U.S. national phase application of International Application No. PCT/EP2003/007228, filed Jul. 7, 2003, which claims the benefit of U.S. Provisional Patent Application No. 60/395,317, filed Jul. 12, 2002.

This invention relates to the use of articles formed of water-absorbent, predominantly open-celled crosslinked acid-functional addition polymer foams in hygiene articles.

Water-absorbent, predominantly open-celled foams based on crosslinked acid-functional monomers are known, cf. EP-B-0 858 478 and WO-A-00/52087. They are prepared for example by foaming a polymerizable aqueous mixture containing at least 50 mol % neutralized acid-functional monoethylenically unsaturated monomers, crosslinkers and at least one surfactant and subsequently polymerizing the foamed mixture. The foaming of the polymerizable mixture can be effected for example by dispersing fine bubbles of a gas which is inert toward free radicals or by dissolving such a gas under elevated pressure in the polymerizable mixture and decompressing the mixture. The water content of the foams is adjusted to 1-60% by weight for example. The foams can optionally be subjected to surface postcrosslinking by spraying a crosslinker onto the foamed material or immersing the foam therein and heating the crosslinker-laden foam to a higher temperature. The foams are used for example in hygiene articles to acquire, distribute and store body fluids.

WO-A-99/44648 likewise discloses predominantly open-celled foams based on crosslinked acid-functional monomers where at least 20 mol % of the acid-functional monomers are neutralized with tertiary alkanolamines and/or the free acid groups of the hydrogel foam are at least 20 mol % neutralized with at least one alkanolamine after polymerization. The hydrogel foams neutralized with alkanolamines are tacky. The tackiness is fully removable by powdering with finely divided powders such as finely divided silicon dioxide, talcum, silicates or starch.

U.S. Pat. No. 4,286,082 discloses water-absorbent polymers obtainable by polymerizing salts of acrylic acid, optionally mixed with acrylic acid, in the presence of a crosslinker and of at least one surface-active agent in an aqueous medium and drying the gellike polymers. The polymers can be powderized and mixed in powder form with 0.01 to 10 parts by weight, based on 100 parts by weight of the pulverulent polymer, of finely divided silicon dioxide. Such mixtures have good processing properties.

U.S. Pat. No. 4,734,478 describes mixtures of pulverulent water-absorbent polymers which have been subjected to a surface postcrosslinking operation and finely divided silicon dioxide. The mixtures remain free flowing and do not clump even in the presence of moisture. They are used in hygiene articles to absorb body fluids.

WO-A-97/31600 discloses an absorber element for use in hygiene or sanitary articles wherein a plurality of elements of a superabsorbent foam are arranged on a support in a grid pattern at such distances that the elements in the swollen state touch at their peripheries. For example, a monomer foam can be applied to the support in the desired grid pattern and then polymerized or separately prepared foam elements can be fixed on the support in the desired grid pattern by chemical or physical means. However, the permeability of the superabsorbent foams is still in need of improvement.

It is an object of the present invention to provide water-absorbent hydrogel foams providing improved acquisition compared with known products.

We have found that this object is achieved according to the invention by the use of articles formed of water-absorbent open-celled crosslinked acid-functional addition polymer foams and containing finely divided silicon dioxide and/or at least one surfactant on their surface as an acquisition and/or distribution layer, in hygiene articles. Said surface of said formed articles is preferably subjected to a postcrosslinking operation by application of at least one crosslinker and heating to temperatures at which said crosslinker reacts with said polymers. This is followed by the treatment with finely divided silicon dioxide and/or at least one surfactant. Formed articles for the purposes of the present invention include for example strands or granules and also preferably sheetlike structures such as sheets, webs or films of predominantly open-celled hydrogel foams. Webs or films from 0.5 to 10 mm in thickness are particularly preferred formed articles. Their surface postcrosslinking and treatment with silicon dioxide and/or at least one surfactant may also have been carried out on just one surface, either on the upper surface or on the lower surface. When such formed articles are used in a hygiene article, that side of the formed articles which has been surface postcrosslinked and treated with silicon dioxide and/or a surfactant is disposed so that it is present on the bodyfacing side as an acquisition layer.

Finely divided silicon dioxide is a commercially available material. It is sold under the AEROSIL trademark for example. The average particle diameter is for example in the range from 1 to 50 µm and is preferably in the range from 2 to 20 µm. Such products have a BET surface area of for example from 100 to 250 m$^2$/g and preferably of from 150 to 200 m$^2$/g. Based on 100 parts by weight of an article formed of a hydrogel foam, finely divided silicon dioxide is used for example in an amount of from 0.01 to 10 parts by weight and preferably of from 0.5 to 4 parts by weight.

Useful surfactants include all surface-active compounds having an HLB value of from 3 to 5 (for the definition of the HLB value cf. W. C. Griffin, Journal of Society of Cosmetic Chemist, Volume 1, 311 (1950)). It is possible to use not only anionic, cationic, amphoteric or nonionic surfactants but also mixtures of mutually compatible surfactants. Useful anionic surfactants include, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, especially the alkali and alkaline earth metal salts, for example sodium, potassium, magnesium, calcium and also ammonium and triethanolamine salts. The alkyl ether sulfates, alkyl ether phosphates and alkyl ether carboxylates may contain from 1 to 10 ethylene oxide or propylene oxide units and preferably from 1 to 3 ethylene oxide units in the molecule.

Useful surfactants include for example sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Useful amphoteric surfactants include for example alkylbetaines, alkylamidopropylbetaines, alkylsulfobetaines, alkyl glycinates, alkyl carboxyglycinates, alkyl amphoacetates or propionates, alkyl amphodiacetates, or dipropionates. It is possible to use for example cocodimethylsulfopropylbetaine, laurylbetaine, cocamidopropylbetaine or sodium cocamphopropionate.

Useful nonionic surfactants include for example the reaction products of aliphatic alcohols or alkylphenols having 6 to 20 carbon atoms in the alkyl chain, which can be linear or branched, with ethylene oxide and/or propylene oxide. The amount of alkylene oxide is about 6-60 mol per one mole of alcohol. Also useful are alkylamine oxides, mono- or dialkylalkanolamides, fatty acid esters of polyethylene glycols, ethoxylated fatty acid amides, alkylpolyglycosides or sorbitan ether esters.

Customary cationic surfactants include for example quaternary ammonium compounds, for example cetyltrimethylamuonium chloride.

The surfactants are preferably applied to the formed foam articles in the form of aqueous solutions. For example, the formed foam articles can be dipped into the aqueous solution or an aqueous solution can be sprayed onto their surface or applied in some other way, for example by knife coating. Based on 100 parts by weight of a formed foam article, the amount of surfactant used is for example in the range from 0.1 to 10 and preferably in the range from 0.5 to 2 parts by weight.

Water-absorbent, predominantly open-celled crosslinked acid-functional addition polymer foams are known from the prior art cited at the beginning, cf. EP-B-0 858 478 page 2 line 55 to page 10 line 54, WO-A-99/44648 page 4 line 41 to page 27 line 42 and WO-A-00/52087 page 5 line 32 to page 28 line 45. They are also known as hydrogel foams and are obtainable for example by first preparing a polymerizable aqueous mixture containing from 10 to 80% by weight of acid-functional monoethylenically unsaturated monomers which are partially neutralized, for example at least 20 mol % neutralized,
optionally up to 50% by weight of other monoethylenically unsaturated monomers,
from 0.001 to 5% by weight of crosslinker,
at least one initiator,
from 0.1 to 20% by weight of at least one surfactant,
optionally a solubilizer and
optionally thickeners, foam stabilizers, polymerization regulators, fillers and/or nucleators.

The polymerizable aqueous mixture is foamed either by dispersing fine bubbles of a gas which is inert toward free radicals or by dissolving an inert gas under a pressure of from 2 to 400 bar and then decompressing the mixture to atmospheric. The foamed mixture is then in either case polymerized to form a hydrogel foam. This method makes it possible to obtain formed foam articles in any shape, although preference is given to blocks from which foam webs or sheets of for example from 0.5 to 10 mm in thickness can be cut, and also to sheets, webs or films. The surface of these formed articles can then be treated with silicon dioxide and/or surfactants or preferably prior to this treatment subjected to a postcrosslinking operation. To postcrosslink the formed foam articles, they are initially treated with a solution of a crosslinker, for example of a polyhydric alcohol such as propylene glycol or butylene glycol, bisepoxides or polyglycidyl compounds, and the crosslinker-solution-treated sheetlike structures formed of predominantly open-celled crosslinked acid-functional addition polymer foams are heated to for example 120-200° C. to postcrosslink the surface, the crosslinkers reacting with the acid groups of the hydrogel foams to form covalent bonds.

Useful acid-functional monoethylenically unsaturated monomers include for example acrylic acid, methacrylic acid, acrylamido-propanesulfonic acid or mixtures thereof. Particular preference is given to the use of acrylic acid as a monomer to prepare water-absorbent addition polymers. The acid-functional compounds are usually neutralized with the aid of aqueous sodium hydroxide solution or potassium hydroxide solution. Neutralization may also be carried out using sodium silicate. Water-absorbent polymers can also be prepared by polymerizing the acid-functional monomers in the presence of natural products such as starch, cellulose, cellulose derivatives or degradation products of starch such as oxidized starch, enzymatically degraded starch or in the presence of acids or bases of destructured starch. Graft polymers are formed. Instead of acid-functional monomers it is also possible to polymerize acrylonitrile or methacrylonitrile in the presence or absence of the above-described natural products and subsequently in either case hydrolyze the nitrile groups to acid groups.

The polymerization of the acid-functional monomers and also of acrylonitrile and methacrylonitrile is always effected in the presence of at least one crosslinker, one initiator and one surfactant in an aqueous medium. These materials are present in the polymerizable aqueous mixture which is foamed for example by the mechanical foaming method (dispersing of fine bubbles of an inert gas into the polymerizable mixture) or by dissolving for example carbon dioxide in the polymerizable aqueous mixture under a pressure of for example 12 bar and decompressing this mixture to atmospheric. The flowable foam thus prepared can then be transferred for example onto a belt having side walls or into molds and polymerized into webs, sheets, films or blocks and subsequently dried. The polymerization is carried out by prior art processes. Depending on the initiator used, it can be effected by raising the temperature, by the action of light (UV rays), by irradiation with electron beams or else by a combination thereof, for example by raising the temperature and UV irradiation.

Foam layers up to 1 mm thick are prepared for example by one sidedly heating or irradiating a polymerizable mixture. To produce sheetlike foam structures more than one centimeter in thickness, the polymerizable mixture is heated by the action of microwaves for preference. Sheetlike structures of foams for example from 1 mm to 5 cm and preferably up to 2 cm in thickness are preferably prepared by initiating the polymerization of the polymerizable foam mixture on both sides, for example by heating the mixture on a belt having side walls while at the same time irradiating the foam from above with UV light. The density of the foam changes only little if at all during the polymerization. The water content of the foams has a major influence on their flexibility. The water content is generally in the range from 1 to 80% by weight and preferably in the range from 5 to 60% by weight.

Foams having particularly high flexibility are obtained when at least 20 mol % of the acid groups of water-absorbent crosslinked acid-functional addition polymer foams have been neutralized with alkanolamines, cf. WO-A-00/52087, page 25 line 1 to page 26 line 10. The degree of neutralization of the carboxyl groups of the hydrogel foams is for example in the range from 40 to 95 mol % and preferably in the range from 55 to 85 mol %. By predominantly open celled is meant that at least 80% of the hydrogel foam is open celled. The hydrogel foams are preferably 100% open celled.

The water-absorbent, predominantly open-celled crosslinked acid-functional polymer foams have for example a density of from 0.001 to 0.9 g/cm$^3$ and preferably of from 0.05 to 0.5 g/cm$^3$, a water absorption capacity of at least 5 g/g, a Free Absorption Rate (FAR) of from 4.0 to 100 g/g sec for a 0.9% by weight aqueous sodium chloride solution and a Vertical Wicking Time (VWT=time for a 0.9% by weight aqueous sodium chloride solution to advance vertically in a foam) of from 0.2 to 120 seconds for a height of 4 cm.

The above-described, prior art sheetlike constructs formed of hydrogel foams may be subjected to a surface postcrosslinking operation on one side or on both sides. The postcrosslinking operation can be carried out not only on the dried but also on the moist hydrogel foam after polymerization. To prepare a sheetlike structure in a hydrogel foam having a postcrosslinking gradient, the foam is fed as a sheetlike structure. This can be effected for example in the form of individual sheets, films, tapes or other sheetlike geometric forms of varying size. For instance, a polyacrylate foam in the form of an endless roll can be subjected to a surface postcrosslinking operation on one side only, on a moving belt, so that an inhomogeneous postcrosslinking takes place in the z direction, where the x and y directions define the area of the surface.

In the inhomogeneous postcrosslinking operation, the crosslinking reagents are applied only to one surface of hydrogel foam, i.e., compounds having at least two reactive groups capable under suitable conditions, for example on heating to not less than 70° C., of reacting with the acid groups of the hydrogel foam. It is also possible in this case to achieve a modification of the inhomogeneous crosslink density by controlling the depthwise penetration of the crosslinker. Suitable crosslinkers combine with the carboxyl groups of the polymer matrix to form covalent or ionic bonds. Such compounds are preferably applied in the form of an aqueous solution to the surface of the sheetlike structure of a hydrogel foam. The aqueous solution can contain for example water-miscible organic solvents, such as alcohols such as methanol, ethanol or isopropanol, acetone, dimethylformamide or dimethyl sulfoxide. Useful crosslinkers include in principle all compounds useful as crosslinkers for preparing hydrogels. Examples of suitable postcrosslinking agents are

- di- or polyglycidyl compounds such as phosphonic acid diglycidyl ether or ethylene glycol diglycidyl ether, bis-chlorohydrin ethers of polyalkylene glycols,
- alkoxysilyl compounds,
- polyaziridines, compounds which contain aziridine units and are based on polyethers or substituted hydrocarbons, for example bis-N-aziridinomethane,
- polyamines or polyamidoamines or their reaction products with epichlorohydrin,
- polyols such as ethylene glycol, 1,2-propanediol, 1,4-butanediol, glycerol, methyltriglycol, polyethylene glycols having an average molecular weight $M_w$ of 200-10 000, di- and polyglycerol, pentaerythritol, trimethylolpropane, sorbitol, the ethoxylates of these polyols, for example glycerol, pentaerythritol and/or trimethylolpropane ethoxylation products containing from 1 to 20 and preferably from 2 to 8 ethylene oxide units per OH group, and also esters thereof with carboxylic acids or carbonic esters such as ethylene carbonate or propylene carbonate,
- carbonic acid derivatives such as urea, thiourea, guanidine, dicyandiamide, 2-oxazolidinone and its derivatives, bisoxazoline, polyoxazolines, di- and polyisocyanates,
- di- and poly-N-methylol compounds such as for example methylenebis(N-methylolmethacrylamide) or melamine-formaldehyde resins,
- compounds having two or more blocked isocyanate groups such as for example trimethylhexamethylene diisocyanate blocked with 2,2,3,6-tetramethyl-4-piperidinone,
- solutions of divalent or more highly valent metal salts of which the metal cations can react with the acid groups of the polymer to form ionic or covalent bonds or complexes. Examples of divalent or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Zn^{2+}$, $Zr^{4+}$, $La^{3+}$ and $Ce^{4+}$. Preferred metal cations used are $Mg^{2+}$, $Ca^{2+}$, $Ba^{2+}$, $Al^{3+}$ and $Zr^{4+}$. The metal cations may be used not only alone but also mixed with each other and also together with at least one other customary crosslinker (cf. above). Of the metal cations mentioned, all metal salts are suitable that possess adequate solubility in the solvent to be used. Of particular suitability are metal salts with weakly complexing anions such as chloride, nitrate and sulfate. Useful solvents for the metal salts include water, alcohols, acetone, dimethylformamide, dimethyl sulfoxide and also mixtures thereof. Particularly preferred solvents are water and water-alcohol mixtures such as water/methanol or water/1,2-propanediol.

If necessary, the postcrosslinking operation can be carried out in the presence of acidic catalysts such as for example p-toluenesulfonic acid, phosphoric acid, boric acid or ammonium dihydrogenphosphate.

Particularly suitable postcrosslinking agents are di- or polyglycidyl compounds such as ethylene glycol diglycidyl ether, the reaction products of polyamidoamines with epichlorohydrin, polyvalent metal cations and 2-oxazolidinone.

In a continuous production process, the crosslinker solution is preferably applied by spraying a solution of the crosslinker for example through parallel connected nozzles which spray onto one surface only of the sheetlike hydrogel foam. The solution of the crosslinker can be applied via any apparatus known to one skilled in the art. It can be augmented for example with compressed air or effected without compressed air. The compressed air is preferably produced using inert carrier gas, for example nitrogen, argon or helium. Furthermore, the area to be impregnated can be determined and set via spray angles. The spray angle can be chosen via an electronically adjustable nozzle opening. The setting of the droplet size of the solution to be sprayed can alternatively be effected via the setting of the viscosity of the crosslinker solution and/or via the compressed air. The surface of the sheetlike structure of hydrogel foam can be provided with the crosslinker homogeneously or—as already indicated above—inhomogeneously. The crosslinker or a solution of the crosslinker can also for example be printed in the form of a pattern onto the surface of the hydrogel foam or be applied in the form of a pattern in any other way. Similarly, onesided application of the crosslinker is possible using a knife coater.

The postcrosslinker solution is applied for example in an amount per unit area which should not exceed 0.02 ml/cm². More preferably, the surface has a postcrosslinker solution rate in the range from 0.001 to 0.015 ml/cm² and most preferably in the range from 0.001 to 0.012 ml/cm². This application rate ensures that the depthwise penetration of the postcrosslinker solution does not exceed the thickness of the sheetlike construct of hydrogel foam, so that a postcrosslinking gradient can develop.

Generally, the postcrosslinker solution is applied in such a concentration that the solvent does not account for more than 50% by weight and the crosslinker quantity for not more than 40% by weight, each based on polymer. Preferably the surface receives a solvent quantity in the concentration range from 0.1 to 30% by weight, more preferably in the concentration range from 0.5 to 20% by weight and most preferably in the concentration range from 1 to 10% by weight, each based on polymer. The crosslinker quantity based on polymer foam is for example in the range from 0.1 to 25% by weight, preferably in the range from 0.5 to 10% by weight and mostly in the range from 0.5 to 8% by weight.

The postcrosslinking gradient can be controlled for example by controlling the depthwise penetration of the crosslinker solution via the application rate and crosslinker quantity depending on the layer thickness of the sheetlike hydrogel foam feed. Both the top surface and the bottom surface of the gel foam can be postcrosslinked, but in that case different amounts of crosslinker must be applied respectively to the top surface and the bottom surface in order that a postcrosslinking gradient is developed between these surfaces. To prepare a sheetlike structure of a hydrogel foam having a postcrosslinking gradient between top surface and bottom surface in accordance with the invention, it is also possible to apply at least one crosslinker or a solution containing at least one crosslinker to the top surface and to the bottom surface of the sheetlike structure in equal amounts, to carry out the postcrosslinking operation and subsequently to split the thus both sidedly surface-postcrosslinked sheetlike structure a single time by for example making a horizontal cut in the z direction of the sheetlike structure. If, for example, the cut is made in the middle of the z direction of the both sidedly postcrosslinked sheetlike structure, it is halved.

After the crosslinker solution has been applied, the crosslinker is reacted with the hydrogel foam, for example in a downstream drying zone, at from 80 to 190° C. and preferably at from 100 to 160° C. The reaction time is for example in the range from 2 minutes to 6 hours, preferably in the range from 10 minutes to 2 hours and mostly in the range from 10 minutes to 1 hour, during which not only cleavage products but also solvent fractions can be removed. The drying and postcrosslinking operation can also be effected by blowing with a preheated carrier gas.

Sheetlike structures formed of a hydrogel foam can be used in hygiene articles directly or after a surficial postcrosslinking operation, which can be carried out on both sides or preferably on one side, and subsequent treatment with silicon dioxide and/or a surfactant, as an acquisition layer and/or distribution layer. In the case of a merely onesided postcrosslinking operation on sheetlike hydrogel foam, there is a crosslink gradient between the upper surface and the lower surface of the sheetlike structure. Such only one sidedly crosslinked sheetlike structures formed of hydrogel foams and treated with silicon dioxide and/or surfactants are preferably used in hygiene articles so that the surface having the higher crosslink density faces the body. Such a structure has distinctly improved properties over homogeneously crosslinked sheetlike samples of the same size which have been subjected to the same treatment with silicon dioxide and/or surfactants with regard to absorption rate and permeability.

Hygiene articles are for example infant diapers, incontinence products, femcare articles, wound contact materials or secondary wound dressings. A hygiene article generally comprises a combination of a liquid-impervious backsheet, a liquid-pervious topsheet, and an absorbent core. Hygiene articles of this kind are known, for example from EP-A-0 689 818. The absorbent core is fixed between the topsheet and the backsheet. Optionally, leg cuffs and self-adhesive tabs can be integrated in the hygiene article. A preferred design for such hygiene articles is known for example from U.S. Pat. No. 3,860,003.

The topsheet is a soft interlayer which does not irritate the skin. The topsheet is water pervious and permits rapid passage into the subsequent absorbent core of the body fluid to be absorbed. The topsheet can be prepared from a multiplicity of different materials, for example porous foams, perforated synthetic films, natural fibers (cellulose, cotton fibers), synthetic fibers (polyester, polypropylene fibers) or a combination of natural and synthetic fibers. Preferably the topsheet is made of hydrophobic material in order that the skin of the user may be protected against prolonged contact with aqueous fluids.

The topsheet can be prepared from different materials, for example as a woven, non-woven, spun or combed fiber blend. Preference is given to using combed fiber blend which is thermally bonded to form the topsheet. The basis weight of the topsheet is preferably in the range from 18 to 25 $g/m^2$, and it has a tensile strength of at least 400 g/cm in the dry state and 55 g/cm in the wet state.

Topsheet and backsheet are joined together in a suitable manner in a production operation known to one skilled in the art. The absorbent core is positioned between topsheet and backsheet.

The backsheet used is usually a liquid-impervious material, for example a polyolefin (e.g., polyethylene backsheets), in order that the clothing of the wearer may be protected against possible leakage.

The open-celled hydrophilic foam formed from crosslinked acid-functional monomers and treated with silicon dioxide and/or surfactants is used within the absorbent core, according to the invention. Owing to their remarkable properties, such as liquid acquisition and transmission and also storage, the sheetlike hydrogel foam gradient-postcrosslinked constructs treated with silicon dioxide and/or surfactants are predestined for use as an acquisition and distribution layer or generally completely as an absorbent core.

When used as an absorbent core, the foams described above can perform various functions in hygiene articles, namely acquisition, distribution and storage. The absorbent core can also contain two or more, for example 3, 4 or 5, sheetlike constructs of hydrogel foams to be used according to the invention.

The individual functions can either be completely performed or be augmented by further constituents, for instance storage can be increased by the addition of superabsorbent granules or acquisition and distribution can be optimized by further constituents such as high loft nonwovens, polypropylene nonwovens, polyester nonwovens or chemically modified pulps.

Determination of Monomer Foam Density

Precisely 100 ml of the monomer foam are introduced into a graduated cylinder and the weight of the foam volume is determined. Dividing the weight found in g by 100 provides the density of the foam in $g/cm^3$.

Determination of the Polymer Foam Density

The density of superabsorbent foams is determined gravimetrically. A uniform foam layer having a defined thickness in the range from 3 to 5 mm is cut for example with a sharp knife to obtain square shapes having an edge length of 5 cm. The samples are weighed and the weight obtained is divided by the volume calculated from the dimensions.

Determination of Absorption Capacity

The absorption capacity of the superabsorbent foam in terms of water per gram of superabsorbent is determined on pieces of foam having a thickness of 3 mm and each weighing 1 g. The absorption capacity is here tested by the teabag test. The liquid used is 0.9% by weight sodium chloride solution. 1 g of the foam material is introduced into a teabag, which is then sealed. Care must be taken to ensure that the teabag offers sufficient room for complete swelling. The teabag is then immersed for a certain period, for example 30 min, into the liquid and weighed back after a drip-off time of for example 10 minutes. The blank is determined by immersing the teabag without superabsorbent foam in the solution and determining the weight of the teabag under the conditions described above. The absorption capacity then follows from the following equation (1):

$$\text{Absorption capacity} = \frac{G_{TS} - G_T}{G_S}, \text{ where} \qquad (1)$$

$G_{TS}$ is the weight of the teabag with superabsorbent foam
$G_T$ is the weight of the teabag in the blank test and
$G_S$ is the starting weight of the superabsorbent foam.

Determination of Absorption Rate

The Free Absorption Rate (FAR) is found by cutting out, using a sharp knife, rectangular samples weighing 0.5 g ($W_1$) from foam layers having a uniform thickness of 3 mm. These samples are placed in a Petri dish and 10 g ($W_2$) of 0.9% sodium chloride solution are poured over. All weights are measured carefully. A stopwatch is used to determine the time required for the foam sample to completely absorb the 0.9% sodium chloride solution. The absorption rate (FAR) in g/g-sec is calculated from the following equation (2):

$$\text{FAR} = W_2/W_1 \times \text{time measured in sec} \qquad (2)$$

Vertical Wicking Time VWT

A Petri dish (10 cm in diameter and 1 cm in height) is filled with 0.9% sodium chloride solution up to a depth of 0.5 cm. A glass tube (1 cm in diameter and 15 cm in length) is then sited a short distance above the base of the dish. A foam strip 6 cm in length having a square base area of 5×5 mm is marked at 2.4 and 6 cm and placed inside the glass tube in the liquid. The time measurement is started at the same time. The time in seconds taken to reach the respective mark is determined.

Acquisition Time

The open-celled polyacrylate foam is cut into layers 1.5 mm, 2 mm or 4 mm in thickness. A commercially available diaper is carefully cut open, the high loft used as an acquisition medium removed and instead the open-celled polyacrylate foam layer inserted. The diaper is resealed. Synthetic urine solution is applied to it through a plastic plate having a ring in the middle (inner diameter of the ring 6.0 cm, height 4.0 cm). The plate is loaded with additional weights so that the total pressure on the diaper is 13.6 g/cm². The plastic plate is placed on the diaper in such a way that the center of the diaper is also the center of the application ring. 60 ml of 0.9% by weight sodium chloride solution are applied three times. The sodium chloride solution is measured out in a graduated cylinder and applied to the diaper in a continuous stream through the ring in the plate. At the same time, the time is taken for the solution to penetrate completely into the diaper. The time measured is noted as acquisition time 1. Thereafter, the diaper is loaded with a plate for 20 min, the pressure being maintained at 13.6 g/cm². This is followed by the second application of the liquid. The time measured is noted as acquisition time 2. The same method is employed to determine acquisition time 3.

The percentages in the examples are by weight, unless the context suggests otherwise.

EXAMPLES

Example 1

(a) Preparation of a Foam Film

The following components were mixed in a beaker using a magnetic stirrer:

| | |
|---|---|
| 348.55 g | of acrylic acid (4.84 mol) |
| 135.51 g | of 37.3% sodium acrylate solution in water (0.54 mol) |
| 28.00 g | of polyethylene glycol diacrylate of polyethylene glycol of molar mass 400 |
| 21.33 g | of a 15% aqueous solution of an addition product of 80 mol of ethylene oxide with 1 mol of a linear saturated $C_{16}C_{18}$ fatty alcohol |
| 65.70 g | of water |

With ice-cooling, 400.90 g (2.69 mol) of triethanolamine were added to this solution in such a way that the internal temperature did not rise above 16° C. The resulting solution was transferred into a pressure vessel and saturated therein with carbon dioxide under a pressure of 12 bar for 25 min. Under pressure, 26.67 g of a 3% aqueous solution of 2,2'-azobis(2-amidinopropane)dihydrochloride were added and mixed in using a fast stream of carbon dioxide until the mixture was homogeneous. Carbon dioxide was then passed through the reaction mixture for a further 5 min. The saturated reaction mixture was forced under a pressure of 12 bar through a 1 mm diameter nozzle to form a finely celled free-flowing foam.

The monomer foam obtained was placed on an A3 size glass plate having edges 3 mm in height and covered with a second glass plate. The foam sample was irradiated synchronously from both sides with two UV/VIS lamps (Höhnle UV 1000) for 4 minutes.

The foam obtained was completely dried in a vacuum oven at 70° C. and subsequently adjusted to a moisture content of 5% by treating with water. 3.7% of amorphous synthetic silica (Sipernat 225 from Degussa AG) was applied to the surface of the foam. The silica adhered to the foam surface. Compared with an untreated foam sample, the silica-treated sample had a higher droplet acquisition rate, cf. table.

| | |
|---|---|
| Solids content of reaction mixture: | 81.04% |
| Degree of neutralization: | 60 mol % |
| Monomer foam density: | 0.18 g/cm³ |
| Polymer foam density: | 0.19 g/cm³ |
| Foam structure: | homogeneous, open celled, no skin |

Example 2

A foam sample prepared according to example 1 in a thickness of 3 mm and having a residual moisture content of 5% was immersed for 30 minutes in a 1% solution of a commercially available modified polymethylsiloxane (Nuwet 100 from OSi) in ethanol. The sample was then dried overnight and the droplet acquisition time determined, cf. table.

Example 3

A foam sample prepared according to example 1 in a thickness of 3 mm and having a residual moisture content of 5% was immersed for 30 minutes in a 1% solution of an addition product of 80 mol of ethylene oxide with 1 mol of a $C_{16}C_{18}$ alcohol in ethanol. The sample was then dried overnight and the droplet acquisition time determined, cf. table.

TABLE

| Example | Time for droplet acquisition [sec] | Assessment of samples |
|---|---|---|
| 1 | 0.7 | hydrophilic |
| 2 | 1 | hydrophilic |
| 3 | 1 | hydrophilic |
| Comparison: untreated foam | 1.5 | hydrophilic |

We claim:

1. A method of preparing a water-absorbent open-celled crosslinked acid-functional hydrogel foam comprising:
   (a) preparing a polymerizable aqueous mixture containing
      (i) from 10 to 80%, by weight, of acid-functional monoethylenically unsaturated monomers which are partially neutralized,
      (ii) optionally up to 50%, by weight, of other monoethylenically unsaturated monomers,
      (iii) from 0.001 to 5%, by weight, of a crosslinker,
      (iv) at least one initiator, and
      (v) from 0.1 to 20%, by weight, of at least one surfactant;
   (b) foaming the polymerizable aqueous mixture of step (a);
   (c) polymerizing the foamed mixture of step (b) to form a hydrogel foam; then
   (d) applying to a surface of the hydrogel foam of step (c) at least one surfactant and optionally a finely divided silicon dioxide, wherein an amount of the surfactant on the surface of the hydrogel foam is in the range from 0.1 to 10% by weight, based on the weight of the foam.

2. The method of claim 1 wherein, prior to step (d), the surface of the hydrogel foam has been subjected to a postcrosslinking operation by application of at least one crosslinker and heating to a temperature at which said crosslinker reacts with the acid-functionality of the hydrogel foam.

3. The method of claim 1 wherein, after step (d), the surface of the hydrogel foam has been subjected to a postcrosslinking operation by application of at least one crosslinker and heating to a temperature at which said crosslinker reacts with the acid-functionality of the hydrogel foam.

4. The method of claim 1 wherein the amount of surfactant applied on the surface of the hydrogel foam is in a range of 0.5 to 2% by weight, based on the weight of the hydrogel foam.

5. The method of claim 1 wherein the hydrogel foam comprises a crosslinked polymer of partially neutralized acrylic acid.

6. The method of claim 1 wherein the polymerizable aqueous mixture of step (a) is foamed in step (b) by
   (i) dispersing fine bubbles of a gas which is inert toward free radicals, or
   (ii) dissolving an inert gas under a pressure of from 2 to 400 bar, then decompressing the mixture to atmospheric.

7. The method of claim 1 wherein the hydrogel foam has a droplet acquisition time for a 0.9%, by weight, sodium chloride solution, in seconds, at least 30% faster than an identical water-absorbent open-celled crosslinked acid-functional addition polymer foam lacking at least one surfactant applied on a surface of the hydrogel.

8. The method of claim 1 wherein a finely divided silicon dioxide is applied to the surface of the hydrogel foam of step (c), and the finely divided silicon dioxide has an average particle size of from 5 to 50 μm and a BET surface area of at least 100 $m^2/g$.

9. The method of claim 8 wherein the amount of silicon dioxide on the surface of the hydrogel foam is in a range from 0.01 to 5% by weight, based on the weight of the hydrogel foam.

* * * * *